(12) United States Patent
Thetford

(10) Patent No.: US 8,133,914 B2
(45) Date of Patent: Mar. 13, 2012

(54) COMPOUNDS AND COMPOSITIONS THEREOF

(75) Inventor: Dean Thetford, Norden (GB)

(73) Assignee: Lubrizol Limited, Hazelwood, Derby (GB)

(*) Notice: Subject to any disclaimer, the term of this patent is extended or adjusted under 35 U.S.C. 154(b) by 154 days.

(21) Appl. No.: 12/440,107

(22) PCT Filed: Sep. 7, 2007

(86) PCT No.: PCT/EP2007/059386
§ 371 (c)(1),
(2), (4) Date: Mar. 5, 2009

(87) PCT Pub. No.: WO2008/028954
PCT Pub. Date: Mar. 13, 2008

(65) Prior Publication Data
US 2010/0035958 A1    Feb. 11, 2010

Related U.S. Application Data

(60) Provisional application No. 60/824,801, filed on Sep. 7, 2006.

(51) Int. Cl.
*A61K 31/4035* (2006.01)
*C07D 209/48* (2006.01)

(52) U.S. Cl. ........ 514/417; 548/469; 548/470; 548/473; 514/415; 514/416

(58) Field of Classification Search .......... 548/469, 548/470, 473; 514/415, 416, 417
See application file for complete search history.

(56) References Cited

U.S. PATENT DOCUMENTS

| | | | | |
|---|---|---|---|---|
| 6,060,215 A | * | 5/2000 | Amanokura et al. | 430/281.1 |
| 7,009,027 B2 | * | 3/2006 | Heinemann et al. | 528/272 |
| 2005/0120911 A1 | | 6/2005 | Huber et al. | |

FOREIGN PATENT DOCUMENTS

| | | |
|---|---|---|
| JP | 7325431 A | 12/1995 |
| WO | 2007/102911 A2 | 9/2007 |

OTHER PUBLICATIONS

A. Ginu et al., Adhesive and Thermal Properties of Epoxy-Imide Resins Obtained from Different Diimide-Diacids: Structure-Property Correlations, International Journal of Polymeric Materials, vol. 55, No. 2, 2006, pp. 121-134.

* cited by examiner

*Primary Examiner* — Golam M M Shameem
(74) *Attorney, Agent, or Firm* — Samuel B. Laferty

(57) ABSTRACT

The invention relates to novel compounds containing a carboxylic acid head group. The invention further provides compositions containing the novel compounds, a particulate solid and an organic medium or water.

12 Claims, No Drawings

COMPOUNDS AND COMPOSITIONS THEREOF

CROSS REFERENCE TO RELATED APPLICATION

This application claims priority from PCT Application Serial No. PCT/EP2007/059386 filed on Sep. 7, 2007, which claims the benefit of U.S. Provisional Application No. 60/824,801 filed on Sep. 7, 2006.

FIELD OF INVENTION

The invention relates to novel compounds containing a carboxylic acid head group. The invention further provides compositions containing the novel compounds, a particulate solid and an organic medium.

BACKGROUND OF THE INVENTION

Dispersants containing terminal acidic groups, such as, carboxylic acid (such as derivatives of 1,2,4-benzenetricarboxylic acid), phosphates and sulphates are known. The phosphate and sulphates are generally, prepared by reaction of a hydroxy ended polymer chain with phosphorus pentoxide, phosphorus oxychloride, polyphosphoric acid or sulphuric acid. The dispersant polymer chains are often derived from polyester or polyalkoxylate chains containing terminal hydroxyl groups. Dispersants known in the art containing terminal acidic groups are suitable for a polar medium, such as, water, ketones, esters and the like. However, it would be advantageous to utilise the dispersant properties of compounds containing terminal acidic groups in both a polar and a non-polar organic medium. The present invention provides such a dispersant and compositions thereof.

U.S. 2005/0120911 and U.S. 2004/0039946 disclose polymeric dispersants prepared from a Jeffamine monoamine and 1,2,4-benzenetricarboxylic acid anhydride and a polyisobutylene amine and 1,2,4-benzenetricarboxylic acid anhydride, respectively. The former agents are used as dispersants on inorganic and organic lake pigments in polar solvents such as ester and alcohols and are not useful in non-polar solvents such as aliphatic mineral oil. The latter agents are used as dispersants in non-polar solvents only and cannot be used in polar solvents.

U.S. Patent Application Ser. No. 60/750,479 discloses polyether amine based dispersants containing a polar inorganic group. The polar inorganic group includes groups such as a sulphur or phosphorus acidic polar head group.

SUMMARY OF THE INVENTION

In one embodiment, the invention provides a compound of Formulae (1) or (2), or salts thereof:

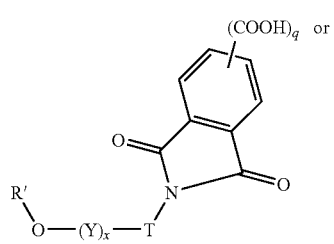

Formula (1)

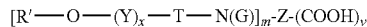

Formula (2)

wherein
T is —(CH$_2$)$_3$— or —CH$_2$CH(CH$_3$)—;
R' is H or C$_{1-50}$-optionally substituted hydrocarbyl, or C$_{1-50}$-optionally substituted hydrocarbonyl;
Y is C$_{2-4}$-alkyleneoxy;
x is 2 to 90;
G is hydrogen, C$_{1-50}$-optionally substituted hydrocarbyl or C$_{1-50}$-optionally substituted hydrocarbonyl, or is the residue of an optionally substituted alkyl (meth)acrylate or (meth)acrylamide, or the residue of an epoxide;
Z is an aromatic moiety;
v is an integer from 1 to 3, such as 1 or 2;
m is 1 or 2, with the proviso that in Formula (2), the sum of (v+m) is 2 to 4; and
q is 1 or 2, with the proviso that in Formula (1), when q is 1, T is —(CH$_2$)$_3$—, and when q is 2, T is —(CH$_2$)$_3$— or —CH$_2$CH(CH$_3$)—.

In one embodiment, the invention provides a composition comprising a particulate solid; either (i) an organic medium, or (ii) water; and a compound of Formulae (1) or (2), or salts thereof:

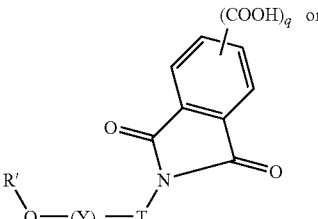

Formula (1)

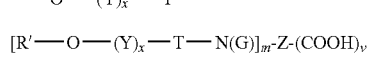

Formula (2)

wherein
T is —(CH$_2$)$_3$— or —CH$_2$CH(CH$_3$)—;
R' is H or C$_{1-50}$-optionally substituted hydrocarbyl, or C$_{1-50}$-optionally substituted hydrocarbonyl;
Y is C$_{2-4}$-alkyleneoxy;
x is 2 to 90;
G is hydrogen, C$_{1-50}$-optionally substituted hydrocarbyl or C$_{1-50}$-optionally substituted hydrocarbonyl, or is the residue of an optionally substituted alkyl (meth)acrylate or (meth)acrylamide, or the residue of an epoxide;
Z is an aromatic moiety;
v is an integer from 1 to 3, such as 1 or 2;
m is 1 or 2, with the proviso that in Formula (2), the sum of (v+m) is 2 to 4; and
q is 1 or 2, with the proviso that in Formula (1), when q is 1, T is —(CH$_2$)$_3$—, and when q is 2, T is —(CH$_2$)$_3$— or —CH$_2$CH(CH$_3$)—.

DETAILED DESCRIPTION OF THE INVENTION

The present invention provides a compound and compositions as disclosed herein above.

As used herein, the term "(meth) acrylic ester or amide group" means methacrylate, acrylate, methacrylamide, acrylamide, or substituted acrylic or methacrylic ester or amide moieties.

In one embodiment, some or all of R' hydrocarbyl groups, the number of carbon atoms on each hydrocarbyl group may be in the range of 1 to 36, or 1 to 20.

In one embodiment, the R' hydrocarbyl groups include aryl, aralkyl, alkaryl, cycloalkyl or alkyl, which may be linear or branched. In one embodiment, the hydrocarbyl group is substituted. In another embodiment, the hydrocarbyl group is unsubstituted.

In one embodiment, R' is aryl. Examples of a suitable aryl group include naphthyl or phenyl.

In one embodiment, R' is aralkyl. Examples of a suitable aralkyl group include 2-phenylethyl or benzyl.

In one embodiment, R' is alkaryl. Examples of a suitable alkaryl group include octyl phenyl or nonyl phenyl.

In one embodiment, R' is cycloalkyl. Examples of a suitable cycloalkyl group include a $C_{3-8}$-cycloalkyl, such as, cyclopropyl or cyclohexyl.

In one embodiment, R' is an optionally branched alkyl, such as a $C_{1-36}$ optionally branched alkyl. R' in other embodiments may be $C_{1-18}$-alkyl, $C_{1-6}$-alkyl, $C_{1-4}$-alkyl, or methyl. In one embodiment, R' may be $C_{12-15}$-alkyl.

The group R'—O— of Formula (1) and Formula (2) may be the residue of an alcohol such as methanol, ethanol, n-propanol, n-butanol, n-hexanol, n-octanol, n-decanol, n-dodecanol, n-tetradecanol, n-hexadecanol, n-octadecanol, isopropanol, isobutanol, tert-butanol, 2-ethylbutanol, 2-ethylhexanol, 3-heptanol, 3,5,5-trimethylhexanol, 3,7-dimethyloctanol and the so-called Guerbet alcohols such as those which are commercially available under the trade name Isofol (ex. Condea GmbH) including mixtures thereof. Specific examples of Guerbet alcohols are Isofol 12, 14T, 16, 18T, 18E, 20, 24, 28, 32, 32T and 36.

When R' is substituted hydrocarbyl, the substituent may be $C_{1-10}$-alkoxy, carbonyl, sulphonyl, carbamoyl, sulphamoyl, halogen, nitrile, ureido, urethane or ester (i.e., —COO— or —OCO—).

The hydrocarbonyl group is substantially similar to a hydrocarbyl group except the hydrocarbonyl group contains a >C=O functional group, typically attached to oxygen of the —O—$(Y)_x$ group.

The chain represented by $(Y)_x$ may contain only one type of $C_{2-4}$-alkyleneoxy repeat unit or it may contain two or more different $C_{2-4}$-alkyleneoxy repeat units. When the chain represented by $(Y)_x$ contains two or more different $C_{2-4}$-alkyleneoxy repeat units, the structure of $(Y)_x$ may be random or block.

In one embodiment, Y is a $C_{3-4}$-alkyleneoxy group, —CH$_2$CH$_2$CH$_2$CH$_2$O— or —CH$_2$CH(CH$_3$)CH$_2$O— or —CH$_2$CH(CH$_3$)O—. In another embodiment, Y is a —CH$_2$CH$_2$CH(CH$_3$)O— or —CH$_2$—CH(CH$_2$—CH$_3$)—O—. In one embodiment, Y is $C_{3-4}$-alkyleneoxy and the chain represented by $(Y)_x$ is —CH$_2$CH$_2$CH$_2$CH$_2$O—, —CH$_2$CH(CH$_3$)O— or —CH$_2$—CH(CH$_2$—CH$_3$)—O—.

In one embodiment, the compound of Formula (1) and/or Formula (2) comprises (i) $C_{3-4}$-alkyleneoxy (e.g., —CH$_3$CH(CH$_3$)O—) repeat units, and (ii) may contain a portion of ethyleneoxy repeat units. The ethyleneoxy repeat units in different embodiments may be present on the chain represented by $(Y)_x$ up to a maximum of 45 wt. % of the chain, or up to 35 wt. % of the chain, or up to 30 wt. % of the chain. In one embodiment, no ethyleneoxy repeat units are present on $(Y)_x$.

In other embodiments, the chain $(Y)_x$ may contain at least 50 wt. %, or at least 75 wt. % of ethyleneoxy repeat units when the compound is required for an aqueous medium, optionally further comprising polar organic liquids.

In one embodiment, the compound of Formula (1) and/or Formula (2) comprises a Y group containing —CH$_2$CH(CH$_3$)O— and the chain represented by $(Y)_x$ may contain up to 45% ethyleneoxy repeat units.

In one embodiment, the compound of Formula (1) and/or Formula (2) comprises a Y group of —CH$_3$CH(CH$_3$)O— and the chain represented by $(Y)_x$ may contain up to 75% ethyleneoxy repeat units.

In one embodiment, the compound of Formula (1) and/or Formula (2) comprises a Y group of comprises 100% of $C_{3-4}$-alkyleneoxy repeat units.

In one embodiment, the compound of Formula (1) and/or Formula (2) comprises a Y group of 100% ethyleneoxy repeat units. Compounds of this type are typically utilised in water-based compositions.

In one embodiment, Y is a mixture of $C_{3-4}$-alkyleneoxy where the chain represented by $(Y)_x$ is in part —CH$_2$CH$_2$CH$_2$CH$_2$O—, —CH$_2$CH(CH$_3$)O— or —CH$_2$—CH(CH$_2$—CH$_3$)—O—, with up to 75% ethyleneoxy repeat units present.

In one embodiment, G comprises the residue of an alkyl (meth)acrylate, or mixtures thereof. In one embodiment, G is an alkyl acrylate, and in another embodiment, G is an alkyl methacrylate. In one embodiment, G is an alkyl acrylamide, and in another embodiment, G is an alkyl methacrylamide.

In one embodiment, G may contain acid or basic containing groups. Therefore, G may be a residue of haloacetic acid, an anhydride, a (meth)acrylate/(meth)acrylamide with carboxylic, amino or phosphate functionality, or from propane/butane sultone. Therefore, G may be represented by the general formula —C(=O)QCO$_2$H, and Q is alkylene or phenylene; or by —CH$_2$CO$_2$H, —CH$_2$CH$_2$CO$_2$H, —CH$_2$CH$_2$C(=O)OCH$_2$CH$_2$CO$_2$H, —CH$_2$CH$_2$C(=O)OCH$_2$CH$_2$OPO$_3$H$_2$; —CH$_2$CH$_2$C(=O)OCH$_2$CH$_2$NMe$_2$, or —CH$_2$CH$_2$CH$_2$—SO$_3$H.

Examples of a suitable alkyl (meth)acrylate or (meth)acrylamide include (meth)acrylate or (meth)acrylamide compounds includes those wherein the alkyl group is methyl, ethyl, propyl, iso-propyl, butyl, pentyl, hexyl, heptyl, octyl, 2-ethylhexyl, nonyl, decyl, dodecyl, tetradecyl, hexadecyl, octadecyl, eicosyl, or mixtures thereof.

When m is 1, Z—(COOH)$_v$ may be the residue of 1,2,4-benzenetricarboxylic acid anhydride or 1,2,4,5-benzenetetracarboxylic di-anhydride.

When m is 2, Z—(COOH)$_v$ may be the residue of 1,2,4,5-benzenetetracarboxylic di-anhydride.

When Z—(COOH)$_v$ is the residue of 1,2,4,5-benzenetetracarboxylic dianhydride, the group R'O—$(Y)_x$-T-N— may be the residue of a polyalkyleneoxide monoalkyl ether monoamine. Monoamine compounds of this type are commercially available as the Jeffamine™ M-series of monoamines from Huntsman Corporation. Specific examples of Jeffamine™ amines are M-600 (9, 0, 600), M-1000 (3, 18, 1000), M-2005 (32, 2, 2000) and M-2070 (10, 31, 2000). The figures in parentheses are approximate repeat units of propylene oxide, ethylene oxide and number-average molecular weight respectively.

When m is 1 and G is directly bonded to Z, the compound of Formula (2) has an imide structure, then the group R'O—$(Y)_x$-T-N— may be the residue of a polyalkyleneoxide monoalkyl ether monoamine (commercially available as the Jeffamine™ M-series of monoamines from Huntsman Corporation).

In one embodiment, the compound of Formula (1) and/or Formula (2) is in the form of a salt. Examples of a suitable salting agent include ammonia, a mono-alcoholamine, such as ethanolamine, N-methyl ethanolamine; or a di-alcoholamine such as diethanolamine or N-methyl diethanolamine; or a tri-alcoholamine such as triethanolamine.

In one embodiment, the compound of Formula (1) is represented by the Formula (1a) or salts thereof:

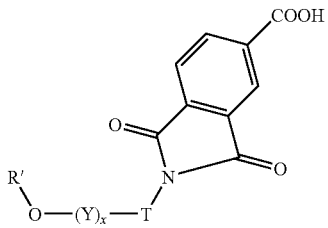

Formula (1a)

wherein

T is —(CH$_2$)$_3$—;

R' is H or C$_{1-50}$-optionally substituted hydrocarbyl, or C$_{1-50}$-optionally substituted hydrocarbonyl;

Y is C$_{2-4}$-alkyleneoxy; and x is 2 to 90.

In one embodiment, the compound of Formula (1) is represented by the Formula (1b) or salts thereof:

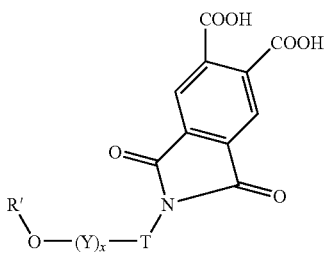

Formula (1b)

wherein

T is —(CH$_2$)$_3$—, or —CH$_2$CH(CH$_3$)—;

R' is H or C$_{1-50}$-optionally substituted hydrocarbyl, or C$_{1-50}$-optionally substituted hydrocarbonyl;

Y is C$_{2-4}$-alkyleneoxy; and x is 2 to 90.

In one embodiment, the compound of Formula (2) is represented by the Formula (2a) or salts thereof:

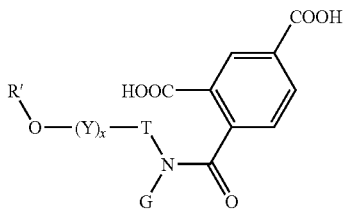

Formula (2a)

In one embodiment, the compound of Formula (2) is represented by the Formula (2b) and/or Formula (2c) or salts thereof:

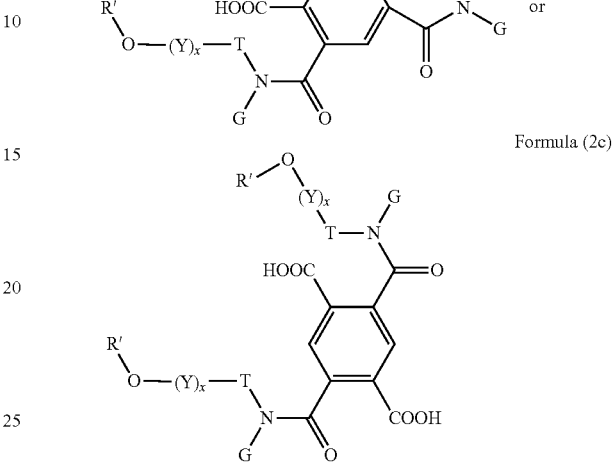

Formula (2b)

or

Formula (2c)

In one embodiment, the compound of Formula (2) is represented by the Formula (2d):

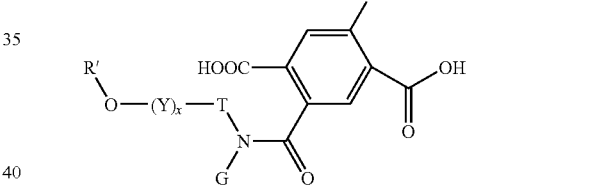

Formula (2d)

For Formula (2a), Formula (2b), Formula (2c) or Formula (2d), T is —(CH$_2$)$_3$— or —CH$_2$CH(CH$_3$)—; R' is H or C$_{1-50}$-optionally substituted hydrocarbyl, or C$_{1-50}$-optionally substituted hydrocarbonyl; Y is C$_{2-4}$-alkyleneoxy; x is 2 to 90; and G is hydrogen, C$_{1-50}$-optionally substituted hydrocarbyl or C$_{1-50}$-optionally substituted hydrocarbonyl, or is the residue of an optionally substituted alkyl (meth)acrylate or (meth)acrylamide, or the residue of an epoxide.

The polymeric dispersant may be prepared, for example, by reacting a polyether amine with (i) 1,2,4-benzenetricarboxylic acid anhydride, or (ii) 1,2,4,5-benzenetetracarboxylic dianhydride. The compound of Formula (1) and/or Formula (2) may be prepared in a one-pot reaction. The polyether amine may be a copolymer of polyethylene oxide and polypropylene oxide depending on the particular type of coating or printing ink system being employed. The reaction is typically carried out at a temperature of at least 90° C. The mixture of a polyoxyalkene amine and 1,2,4-benzenetricarboxylic acid anhydride (and/or 1,2,4,5-benzenetetracarboxylic dianhydride) is stirred continuously and heated for a time ranging between 30 minutes and 10 hours, or for a period of about 2 hours.

When preparing an imide compound of Formula (1) and/or Formula (2), the mixture is typically stirred at a temperature of 100° C. to 180° C., or at a temperature of 100° C. to 120°

C. The temperature of the mixture is then raised up to 220° C., or up to 160° C., and maintained at this temperature for one hour, up to 10 hours. The mixture is then allowed to slowly cool to room temperature.

For a compound of Formula (2) and when G is hydrogen, the mixture is typically stirred at a temperature typically in the range of 40° C. to 100° C., thus reducing the possibility of forming an imide structure.

INDUSTRIAL APPLICATION

In one embodiment, the compound of Formula (1) and/or Formula (2) is a dispersant.

The particulate solid present in the composition may be any inorganic or organic solid material which is substantially insoluble in the organic medium. In one embodiment, the particulate solid is a pigment.

In one embodiment, the composition of the invention provides a paint or ink comprising a particulate solid, an organic liquid, a binder and a compound of Formula (1) and/or Formula (2), or salts thereof.

In one embodiment, the composition of the invention provides improved viscosity and gloss for printing inks and coatings and cosmetic applications, which contain high concentrations of laked pigments. Laked pigments as used herein are precipitated salts of pigments containing sulphonic acid and/or carboxylic acid groups precipitated with an alkaline-earth metal or manganese. In high concentrations laked pigments can affect viscosity, gloss and stability of the printing inks and dispersions. Laked pigments include the following pigments: Beta Napthol Pigment Lakes such as Pigment Red 49 (Red 49:1 and Red 49:2), Red 50:1, Red 51, Red 53 (Red 53:1 and Red 53:3), Red 68, Orange 16, Orange 17:1, Orange 46; BONA Pigment Lakes such as Red 48:1, Red 48:2, Red 48:3, Red 48:4, Red 48:5, Red 52:1, Red 52:2, Red 57:1, Red 58:2, Red 58:4, Red 63:1, Red 63:2, Red 64, Red 64:1, Red 200, Brown 5; Napthol AS Pigment Lakes such as Red 151, Red 237, Red 239, Red 240, Red 243, Red 247, Naphthalene Sulphonic Acid Pigment Lakes such as Yellow 104, Orange 19, Red 60, Red 66, or Red 67.

In one embodiment, the solid is an organic pigment from any of the recognised classes of pigments described, for example, in the Third Edition of the Colour Index (1971) and subsequent revisions of, and supplements thereto, under the chapter headed "Pigments". Carbon black, although strictly inorganic, behaves more like an organic pigment in its dispersing properties.

Examples of suitable solids are pigments for solvent inks; pigments, extenders and fillers for paints and plastics materials; disperse dyes; optical brightening agents and textile auxiliaries for solvent dyebaths, inks and other solvent application systems; solids for oil-based and inverse-emulsion drilling muds; dirt and solid particles in dry cleaning fluids; particulate ceramic materials; magnetic materials and magnetic recording media; fibres such as glass, steel, carbon and boron for composite materials.

Inorganic solids include: extenders and fillers such as talc, kaolin, silica, barytes and chalk; particulate ceramic materials such as alumina, silica, zirconia, titania, silicon nitride, boron nitride, silicon carbide, boron carbide, mixed silicon-aluminium nitrides and metal titanates; particulate magnetic materials such as the magnetic oxides of transition metals, especially iron and chromium, e.g. gamma-$Fe_2O_3$, $Fe_3O_4$, and cobalt-doped iron oxides, calcium oxide, ferrites, especially barium ferrites; and metal particles, especially metallic iron, nickel, cobalt, copper and alloys thereof.

The organic medium present in the composition of the invention in one embodiment is a plastics material and in another embodiment an organic liquid. The organic liquid may be a non-polar or a polar organic liquid, although a polar organic liquid is typically used. By the term "polar" in relation to the organic liquid, it is meant that an organic liquid is capable of forming moderate to strong bonds as described in the article entitled "A Three Dimensional Approach to Solubility" by Crowley et al. in Journal of Paint Technology, Vol. 38, 1966, at page 269. Such organic liquids generally have a hydrogen bonding number of 5 or more as defined in the abovementioned article.

Examples of suitable polar organic liquids are amines, ethers, especially lower alkyl ethers, organic acids, esters, ketones, glycols, alcohols and amides. Numerous specific examples of such moderately strongly hydrogen bonding liquids are given in the book entitled "Compatibility and Solubility" by Ibert Mellan (published in 1968 by Noyes Development Corporation) in Table 2.14 on pages 39-40 and these liquids all fall within the scope of the term polar organic liquid as used herein.

In one embodiment, polar organic liquids include dialkyl ketones, alkyl esters of alkane carboxylic acids and alkanols, especially such liquids containing up to, and including, a total of 6 or 8 carbon atoms. As examples of the polar organic liquids include dialkyl and cycloalkyl ketones, such as acetone, methyl ethyl ketone, diethyl ketone, di-isopropyl ketone, methyl isobutyl ketone, di-isobutyl ketone, methyl isoamyl ketone, methyl n-amyl ketone and cyclohexanone; alkyl esters such as methyl acetate, ethyl acetate, isopropyl acetate, butyl acetate, ethyl formate, methyl propionate, methoxy propylacetate and ethyl butyrate; glycols and glycol esters and ethers, such as ethylene glycol, 2-ethoxyethanol, 3-methoxypropylpropanol, 3-ethoxypropylpropanol, 2-butoxyethyl acetate, 3-methoxypropyl acetate, 3-ethoxypropyl acetate and 2-ethoxyethyl acetate; alkanols such as methanol, ethanol, n-propanol, isopropanol, n-butanol and isobutanol and dialkyl and cyclic ethers such as diethyl ether and tetrahydrofuran. In one embodiment, solvents are alkanols, alkane carboxylic acids and esters of alkane carboxylic acids.

Examples of organic liquids, which may be used as polar organic liquids are film-forming resins such as are suitable for the preparation of inks, paints and chips for use in various applications such as paints and inks. Examples of such resins include polyamides, such as Versamid™ and Wolfamid™, and cellulose ethers, such as ethyl cellulose and ethyl hydroxyethyl cellulose, nitrocellulose and cellulose acetate butyrate resins, including mixtures thereof. Examples of paint resins include short oil alkyd/melamine-formaldehyde, polyester/melamine-formaldehyde, thermosetting acrylic/melamine-formaldehyde, long oil alkyd, polyether polyols and multi-media resins such as acrylic and urea/aldehyde.

The organic liquid may be a polyol, that is to say, an organic liquid with two or more hydroxy groups. In one embodiment, polyols include alpha-omega diols or alpha-omega diol ethoxylates.

In one embodiment, non-polar organic liquids are compounds containing aliphatic groups, aromatic groups or mixtures thereof. The non-polar organic liquids include non-halogenated aromatic hydrocarbons (e.g., toluene and xylene), halogenated aromatic hydrocarbons (e.g., chlorobenzene, dichlorobenzene, chlorotoluene), non-halogenated aliphatic hydrocarbons (e.g., linear and branched aliphatic hydrocarbons containing six or more carbon atoms both fully and partially saturated), halogenated aliphatic hydrocarbons (e.g., dichloromethane, carbon tetrachloride, chloroform, trichloroethane) and natural non-polar organics (e.g., vegetable oil, sunflower oil, linseed oil, terpenes and glycerides).

In one embodiment, the organic liquid comprises at least 0.1% by weight, or 1% by weight or more of a polar organic liquid based on the total organic liquid.

The organic liquid optionally further comprises water. In one embodiment, the organic liquid is free of water.

When the organic liquid contains water, the amount present in one embodiment is not greater than 70%, or not greater than 50%, or not greater than 40% by weight based on the amount of organic liquid.

The plastics material may be a thermoset resin or a thermoplastic resin. The thermosetting resins useful in this invention include resins which undergo a chemical reaction when heated, catalysed, or subject to UV radiation and become relatively infusible. Typical reactions in thermosetting resins include oxidation of unsaturated double bonds, reactions involving epoxy/amine, epoxy/carbonyl, epoxy/hydroxyl, polyisocyanate/hydroxy, amino resin/hydroxy moieties, free radical reactions or polyacrylate, cationic polymerization or epoxy resins and vinyl ether, or condensation of silanol.

Polymers with hydroxy functionality (frequently polyols) are widely used in thermosetting system to crosslink with amino resins or polyisocyanates. The polyols include acrylic polyols, alkyd polyols, polyester polyols, polyether polyols and polyurethane polyols. Typical amino resins include melamine formaldehyde resins, benzoguanamine formaldehyde resins, urea formaldehyde resins and glycoluril formaldehyde resins. Polyisocyanates are resins with two or more isocyanate groups, including both monomeric aliphatic diisocyanates, monomeric aromatic diisocyanates; and their polymers. Typical aliphatic diisocyanates include hexamethylene diisocyanate, isophorone diisocyanate and hydrogenated diphenylmethane diisocyanate. Typical aromatic isocyanates include toluene diisocyanates and biphenylmethane diisocyanates.

In one embodiment, thermoplastic resins include polyolefins, polyesters, polyamides, polycarbonates, polyurethanes, polystyrenics, poly(meth)acrylates, celluloses and cellulose derivatives. Said compositions may be prepared in a number of ways but melt mixing and dry solid blending are typical methods.

If desired, the compositions may contain other ingredients, for example, resins (where these do not already constitute the organic medium), binders, fluidising agents anti-sedimentation agents, plasticisers, surfactants, anti-foamers, rheology modifiers, levelling agents, gloss modifiers and preservatives.

The compositions typically contain from 1 to 95% by weight of the particulate solid, the precise quantity depending on the nature of the solid and the quantity depending on the nature of the solid and the relative densities of the solid and the polar organic liquid. For example, a composition in which the solid is an organic material, such as an organic pigment, in one embodiment contains from 15 to 60% by weight of the solid whereas a composition in which the solid is an inorganic material, such as an inorganic pigment, filler or extender, in one embodiment contains from 40 to 90% by weight of the solid based on the total weight of composition.

The composition may be prepared by any of the conventional methods known for preparing dispersions. Thus, the solid, the organic medium and the dispersant may be mixed in any order, the mixture then being subjected to a mechanical treatment to reduce the particles of the solid to an appropriate size, for example, by ball milling, bead milling, gravel milling or plastic milling until the dispersion is formed. Alternatively, the solid may be treated to reduce its particle size independently or in admixture with either the organic medium or the dispersant, the other ingredient or ingredients then being added and the mixture being agitated to provide the composition.

The composition of the present invention is particularly suited to liquid dispersions. In one embodiment, such dispersion compositions comprise:

(a) 0.5 to 40 parts of a particulate solid;
(b) 0.5 to 30 parts of a compound of Formula (1) and/or Formula (2); and
(c) 30 to 99 parts of an organic liquid; wherein all parts are by weight and the amounts (a)+(b)+(c)=100.

In one embodiment, component a) comprises 0.5 to 40 parts of a pigment and such dispersions are useful as liquid inks, paints and mill-bases.

If a composition is required comprising a particulate solid and a compound of Formula (1) and/or Formula (2) in dry form, the organic liquid is typically volatile so that it may be readily removed from the particulate solid by a simple separation means such as evaporation. In one embodiment, the composition comprises the organic liquid.

If the dry composition consists essentially of the compound of Formula (1) and/or Formula (2) and the particulate solid, it typically contains at least 0.2%, at least 0.5% or at least 1.0% the compound of Formula (1) and/or Formula (2) based on weight of the particulate solid. In one embodiment, the dry composition contains not greater than 100%, not greater than 50%, not greater than 20%, or not greater than 10% by weight of the compound of Formula (1) and/or Formula (2) based on the weight of the particulate solid. In one embodiment, the compound of Formula (1) and/or Formula (2) is present at 0.6 wt % to 8 wt %.

As disclosed hereinbefore, the compositions of the invention are suitable for preparing mill-bases wherein the particulate solid is milled in an organic liquid in the presence of a compound of Formula (1) and/or Formula (2), or salts thereof.

Thus, according to a still further embodiment of the invention, there is provided a mill-base comprising a particulate solid, an organic liquid and a compound of Formula (1) and/or Formula (2), or salts thereof.

Typically, the mill-base contains from 20 to 70% by weight particulate solid based on the total weight of the mill-base. In one embodiment, the particulate solid is not less than 10 or not less than 20% by weight of the mill-base. Such mill-bases may optionally contain a binder added either before or after milling.

The binder is a polymeric material capable of binding the composition on volatilisation of the organic liquid.

Binders are polymeric materials including natural and synthetic materials. In one embodiment, binders include poly(meth)acrylates, polystyrenics, polyesters, polyurethanes, alkyds, polysaccharides such as cellulose, and natural proteins such as casein. In one embodiment, the binder is present in the composition at more than 100% based on the amount of particulate solid, more than 200%, more than 300% or more than 400%.

The amount of optional binder in the mill-base can vary over wide limits but is typically not less than 10%, and often not less than 20% by weight of the continuous/liquid phase of the mill-base. In one embodiment, the amount of binder is not greater than 50% or not greater than 40% by weight of the continuous/liquid phase of the mill-base.

The amount of dispersant in the mill-base is dependent on the amount of particulate solid but is typically from 0.5 to 5% by weight of the mill-base.

Dispersions and mill-bases made from the composition of the invention are particularly suitable for use in coatings and paints both solvent-based and water-based, especially high solids paints; inks, especially offset, flexographic, gravure, radiation-curable, and screen inks; non-aqueous ceramic processes, especially tape-coating, doctor-blade, extrusion and injection moulding type processes, composites, cosmetics, adhesives and plastics materials.

The following examples provide illustrations of the invention. These examples are non exhaustive and are not intended to limit the scope of the invention.

EXAMPLES

Preparative Example 1

(PREP1): 1,2,4-Benzenetricarboxylic acid anhydride (5.03 g, 26.2 mmols) is added to stirred a polyether amine (consisting of C12-15 alcohol reacted with butylene oxide (MW 1700), followed by base catalysed addition of the resultant polyetheralcohol to acrylonitrile and subsequent hydrogenation to give an amine (80% active)) (67.4 g, 26.2 mmols) at 120° C. under a nitrogen atmosphere. The whole mixture is stirred at 120° C. for 2 hours until the anhydride substantially dissolves. The mixture is then heated to 160° C. and held for 1 hour to give upon cooling, an amber liquid (53 g). IR showed no anhydride peak, Acid value is 23.9 mg KOH/g. This is Dispersant 1.

Preparative Example 2

(PREP2): 1,2,4-Benzenetricarboxylic acid anhydride (4.14 g, 21.5 mmols) is added to a stirred polyether amine (consisting of C12-15 alcohol reacted with propylene oxide (MW 1660), followed by base catalysed addition of the resultant polyetheralcohol to acrylonitrile and subsequent hydrogenation to give an amine (85% active)) (50 g, 21.5 mmols) at 120° C. under a nitrogen atmosphere. The whole mixture is stirred at 120° C. for 2 hours until the anhydride substantially dissolves. The mixture is then heated to 160° C. and held for 1 hour to give upon cooling, an amber liquid (53 g). IR showed no anhydride peak, Acid value is 27.7 mg KOH/g. This is Dispersant 2.

Preparative Example 3

(PREP3): 1,2,4-Benzenetricarboxylic acid anhydride (7.24 g, 37.7 mmols) is added to a stirred polyether amine (consisting of methanol reacted with ethylene oxide and propylene oxide (Mw 1800), followed by base catalysed addition of the resultant polyetheralcohol to acrylonitrile and subsequent hydrogenation to give an amine (85% active)) (50 g, 37.7 mmols) at 120° C. under a nitrogen atmosphere. The whole mixture is stirred at 120° C. for 2 hours until the anhydride substantially dissolves. The mixture is then heated to 160° C. for 1 hour to give upon cooling, an amber liquid (55 g). IR showed no anhydride peak, Acid value is 41 mg KOH/g. This is Dispersant 3.

Preparative Example 4

(PREP4): 1,2,4-Benzenetricarboxylic acid anhydride (15.8 g 82.3, mmols) is added to a stirred polyether amine (consisting of methanol reacted with ethylene oxide and propylene oxide (Mw 550), followed by base catalysed addition of the resultant polyetheralcohol to acrylonitrile and subsequent hydrogenation to give an amine) (50 g 82.3, mmols) at 120° C. under a nitrogen atmosphere. The whole mixture is stirred at 120° C. for 2 hours until the anhydride substantially dissolves. The mixture is then heated to 160° C. and held for 1 hour to give upon cooling, an amber liquid (62 g). IR showed no anhydride peak, Acid value is 72.3 mg KOH/g. This is Dispersant 4.

Preparative Example 5

(PREP5): 1,2,4-Benzenetricarboxylic acid anhydride (4.8 g, 25 mmols) is added to a stirred Jeffamine D2000 (50 g, 25 mmols) at 120° C. under a nitrogen atmosphere. The whole mixture is stirred at 120° C. for 2 hours until anhydride substantially dissolves. The mixture is then heated to 160° C. for 1 hour to give upon cooling, an amber liquid (53 g). IR showed no anhydride peak, Acid value is 26.4 mg KOH/g. This is Dispersant 5.

Preparative Example 6

(PREP6): Dimethylaminoethylacrylate (3.19 g, 21.5 mmols), 2,6-di-t-butyl-4-methyl phenol (0.05 g) and a polyether amine (consisting of C12-15 alcohol reacted propylene oxide (MW 1660), followed by base catalysed addition of the resultant polyetheralcohol to acrylonitrile and subsequent hydrogenation to give an amine (85% active)) (50 g, 21.5 mmols) is stirred at 70° C. for 4 hours under an air atmosphere to form a stirred product. 1,2,4,5-Benzenetetracarboxylic dianhydride (2.35 g, 10.8 mmols) is added to the stirred product, followed by heating to 120° C. under a nitrogen atmosphere. The whole mixture is stirred at 120° C. for 3 hours until the anhydride substantially dissolves. The mixture is then heated to 160° C. for 4 hours to give upon cooling, a hazy orange, viscous liquid (54 g). IR showed no anhydride peak, Acid value is 25.3 mg KOH/g. This is Dispersant 6.

Preparative Example 7

(PREP7): Dimethylaminoethylacrylate (3.42 g, 23.1 mmols), 2,6-di t-butyl-4-methyl phenol (0.05 g) and Jeffamine M2005 (50 g, 23.1 mmols) is stirred at 70° C. for 4 hours under an air atmosphere to form a stirred product. 1,2,4-Benzenetricarboxylic acid anhydride (4.44 g, 23.1 mmols) was added to the stirred product, followed by heating to 120° C. under a nitrogen atmosphere. The whole mixture is stirred at 120° C. for 3 hours until the anhydride substantially dissolves. The mixture is then heated to 160° C. for 4 hours to give upon cooling, a hazy orange, viscous liquid (55 g). IR showed no anhydride peak, Acid value is 40.7 mg KOH/g. This is Dispersant 7.

Preparative Example 8

(PREP8): Dimethylaminoethylacrylate (3.19 g, 21.5 mmols), 2,6-di t-butyl-4-methyl phenol (0.05 g) and polyether amine (consisting of C12-15 alcohol reacted propylene oxide (MW 1660), followed by base catalysed addition of the resultant polyetheralcohol to acrylonitrile and subsequent hydrogenation to give an amine (85% active)) (50 g, 21.5 mmols) are stirred at 70° C. for 4 hours under an air atmosphere to form a stirred product. 1,2,4-Benzenetricarboxylic acid anhydride (4.44 g, 23.1 mmols) is added to the stirred product, followed by heating to 120° C. under a nitrogen atmosphere. The whole mixture is then stirred at 120° C. for 3 hours until the anhydride substantially dissolves. The mixture is then heated to 160° C. for 4 hours to give upon cooling, a hazy orange, viscous liquid (55 g). IR showed no anhydride peak, Acid value is 38.2 mg KOH/g. This is Dispersant 8.

Comparative Example 1 (CE1) is Example 1 of U.S. Patent Application 2005/0120911.

Mill-Base Compositions

A series of mill-bases are prepared by utilising Dispersants 1 to 8, and Comparative Example 1.

Mill Base Series 1 (Examples 1 to 9)—Irgalite Rubine L4BD

Dispersant (0.15 g) is dissolved in a solvent (7.85 g of Toluene, or Paraset 29L, or a 4:1 methoxypropylacetate:butanol mixture) in an 8 dram trident vial. 17 g of 3 mm glass beads is added. A Irgalite Rubine L4BD (ex Ciba, Pigment Red 57.1) pigment (2 g) is added to the vial which is capped and sealed. The vial is shaken on a horizontal shaker for 16 hours. The agent's performance is evaluated by subjective assessment of the mill base fluidity and changes in viscosity on standing. The resulting dispersions were then assessed for fluidity using an arbitrary scale of A to E (good to bad). The results obtained are shown in Table 1.

A comparative example is (CE2) is prepared in the absence of dispersant.

Mill Base Series 2 (Examples 11 to 17)—Titanium Dioxide

A dispersant (0.2 g) is dissolved in a solvent (2.3 g of Paraset 29L or a 4:1 methoxypropylacetate:butanol mixture) in an 8 dram trident vial. 17 g of 3 mm glass beads is added. A pigment (Titanium Dioxide TR92, ex Huntsman) (7.5 g) is added to the vial which is capped and sealed. The vial is shaken on a horizontal shaker for 16 hours. The agent's performance is evaluated in a similar manner to Mill Base Series 1. A comparative example is (CE3) is prepared in the absence of dispersant. The results are shown in Table 2.

TABLE 1

| Series 1: Mill Base Examples | Dispersant | Toluene | Paraset 29L | 4:1 MPA:Butanol |
|---|---|---|---|---|
| 1 | 1 | A | A | A/B |
| 2 | 2 | A | A | A |
| 3 | 3 | A/B | | A/B |
| 4 | 4 | A | | A |
| 5 | 5 | C | D | C/D |
| 6 | 6 | A | A | B |
| 7 | 7 | A | C/D | A |
| 8 | 8 | A | A | A/B |
| 9 | CE1 | A | C/D | A |
| 10 | CE2 | E | E | E |

TABLE 2

| Examples | Dispersant | Paraset 29L | 4:1 MPA:Butanol |
|---|---|---|---|
| 11 | 1 | A | A/B |
| 12 | 2 | A | A |
| 13 | 3 | E | A |
| 14 | 4 | E | A |
| 15 | 5 | D/E | E |
| 16 | CE1 | D/E | A |
| 17 | CE3 | E | E |

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A composition comprising a compound of Formulae (1) or salts thereof:

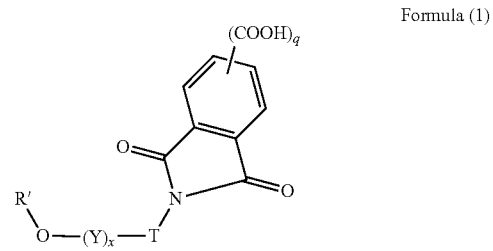

Formula (1)

wherein

T is —(CH$_2$)$_3$— or —CH$_2$CH(CH$_3$)—;

R' is H or C$_{1-50}$-optionally substituted hydrocarbyl, or C$_{1-50}$-optionally substituted hydrocarbonyl;

Y is C$_{2-4}$-alkyleneoxy;

x is 2 to 90;

q is 2.

2. The composition of claim 1, wherein the compound of Formula (1) is represented by Formula (1b), or salts thereof:

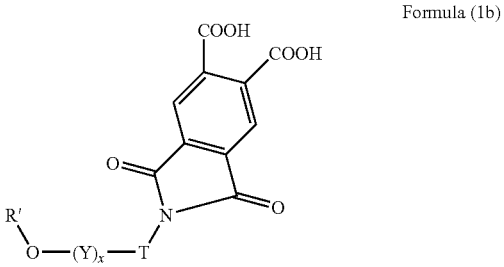

Formula (1b)

wherein T is —(CH$_2$)$_3$—, or —CH$_2$CH(CH$_3$)—; R' is H or C$_{1-50}$-optionally substituted hydrocarbyl, or C$_{1-50}$-optionally substituted hydrocarbonyl; Y is C$_{2-4}$-alkyleneoxy; and x is 2 to 90.

3. The composition of claim 1, wherein Y of the compound of Formulae (1) comprises (i) a portion of C$_{3-4}$-alkyleneoxy repeat units, and (ii) a portion of ethyleneoxy repeat units.

4. The composition of claim 1, wherein Y of the compound of Formulae (1) comprises 100% of —CH$_2$—CH(CH$_3$)O— repeat units.

5. The composition claim 1, wherein Y of the compound of Formulae (1) comprises 100% of $C_{3-4}$-alkyleneoxy repeat units.

6. A composition according to claim 1 further comprising a particulate solid and either (i) an organic medium, or (ii) water.

7. The composition as claimed in claim 6 wherein the organic medium is an organic liquid or a plastics material.

8. The composition as claimed in claim 6 wherein the organic liquid comprises at least 0.1% by weight of a polar organic liquid based on the total organic liquid.

9. The composition as claimed in claim 6, wherein the particulate solid is a pigment.

10. A paint, ink, plastic or cosmetic composition comprising a particulate solid; either (i) an organic medium or (ii) water; and the compound of Formulae (1) as defined in claim 1, or salts thereof.

11. The composition of claim 2, wherein R' is a $C_{12-15}$-alkyl.

12. The composition of claim 11, wherein Y of the compound of Formulae (1b) comprises 100% of $C_{3-4}$-alkyleneoxy repeat units.

* * * * *